(12) United States Patent
Cervino

(10) Patent No.: US 8,329,628 B2
(45) Date of Patent: Dec. 11, 2012

(54) BIODEGRADABLE PERSONAL CLEANSING COMPOSITIONS AND METHODS RELATING TO SAME

(76) Inventor: Kim Cervino, Milford, NJ (US)

( * ) Notice: Subject to any disclaimer, the term of this patent is extended or adjusted under 35 U.S.C. 154(b) by 0 days.

(21) Appl. No.: 13/104,149

(22) Filed: May 10, 2011

(65) Prior Publication Data

US 2011/0275550 A1    Nov. 10, 2011

Related U.S. Application Data

(60) Provisional application No. 61/333,147, filed on May 10, 2010.

(51) Int. Cl.
*C11D 3/382* (2006.01)
*C11D 1/00* (2006.01)
*C11D 3/37* (2006.01)
*A61K 8/04* (2006.01)
*A61K 8/97* (2006.01)

(52) U.S. Cl. ........ 510/139; 510/130; 510/135; 510/155; 510/426; 510/433; 510/441; 510/463; 510/492; 510/499; 424/401; 424/419; 424/485; 424/491; 424/496; 424/500; 424/70.11; 424/70.22

(58) Field of Classification Search .................. 510/130, 510/135, 139, 155, 426, 433, 441, 463, 492, 510/499; 424/401, 419, 485, 491, 496, 500, 424/70.11, 70.22
See application file for complete search history.

(56) References Cited

U.S. PATENT DOCUMENTS

| 6,265,368 | B1 * | 7/2001 | Aronson et al. | 510/403 |
| 2005/0201965 | A1 | 9/2005 | Kuhlman et al. | |
| 2006/0189495 | A1 * | 8/2006 | LiBrizzi et al. | 510/130 |
| 2007/0041927 | A1 * | 2/2007 | Blaeser et al. | 424/70.27 |
| 2008/0031842 | A1 | 2/2008 | Kuhlman et al. | |

OTHER PUBLICATIONS

"EcoSoft and EcoScrub: New Green Technology." Presperse. Biodegradable Exfoliant, Binder Powders. http://www.cosmeticsandtoiletries.com/formulating/ingredient/aids/92620894.html, May 2, 2010.

* cited by examiner

*Primary Examiner* — Brian P Mruk

(57) ABSTRACT

A personal cleansing composition includes a surfactant, a thickener, emulsifier and at least one particulate dispersed in the thickener, the at least one particulate being formed of a substantially biodegradable substance. The at least one particular may include a soy meal based polymer. The soy meal based polymer is both stable and biodegradable. The at least one particulate includes a group of suspended particles added to mechanically scrub the skin of a user or used as a textural ingredient to modify the feel, spreadability or slip of a product. The soy meal based polymer is useful in personal cleansing compositions as an exfoliant, a scrub, a film former or as a filler. The half-life of the composition may be modified as necessary based on the shelf-life of the product.

16 Claims, 1 Drawing Sheet

BIODEGRADABLE PERSONAL CLEANSING COMPOSITIONS AND METHODS RELATING TO SAME

CROSS-REFERENCE TO RELATED APPLICATIONS

This application claims the benefit under 35 U.S.C. §119 (e) of U.S. Provisional Application No. 61/333,147 filed May 10, 2010, which is hereby incorporated by reference in its entirety as part of the present disclosure as if fully set forth herein.

FIELD

The invention is directed to lathering, personal cleansing, and compositions providing superior cleansing with biodegradable components. In addition, the invention is directed to compositions for personal cleansing having biodegradable particulate.

BACKGROUND

Personal cleansing compositions are popular for their ability to remove dirt, oil and debris (e.g. make-up) from the skin or hair of the consumer. Typical surfactant-based cleansers are formulated to provide a specific cleansing power, feel, mildness and lather volume. Each criterion is significant in the desirability of the cleansing product. For example, lather volume is significant as one factor in determining the efficacy and reach of the product. Moreover, ideal personal cleansers should gently cleanse the skin or hair of the user without causing undesirable irritation or leaving the skin dry. Other ingredients may be added to the surfactant-based composition to aid in the cleansing process.

In some compositions, suspended particles are introduced to gently exfoliate the skin and/or teeth and remove oil, dirt, dead skin and other debris. These suspended particles (hereinafter referred to as "particulate") are added to mechanically scrub the skin or teeth of the consumer to aid in the cleansing process. Many personal care companies rely on polyethylene particulate in their facial and body cleansing products. The current polyethylene particulate is recyclable but not biodegradable. After using a personal cleansing product, the consumer typically washes the skin with water. As a result, several hundred thousand pounds of polyethylene particulate is washed down the drain each year. After the product is used and discarded, the particulate typically reaches landfills and the oceans where it creates an undesirable environmental impact. Moreover, polyethylene particulates typically have an unpleasant odor that needs to be masked when making facial and body cleansing products.

It is therefore an object of the present invention to provide personal cleansing compositions useful for cleansing the skin, hair and teeth.

It is also an object of the present invention to provide a personal cleansing composition that includes a pleasant odor profile.

It is another object of the present invention to provide personal cleansing compositions utilizing biodegradable particulate for superior cleansing while being environmentally safe for discarding down the drain.

These and other objects of this invention will become apparent in light of the following disclosure.

BRIEF SUMMARY

In some embodiments, a personal cleansing composition includes a surfactant, a thickener and particulate. The surfactant may generate a foam or lather to disperse the material to be cleansed or disinfected, increasing its surface area and enhancing its contact. The thickener or thickening agent may provide body, increase stability of the composition or improve the suspension of particulate. Other additives such as perfumes, dyes, enzymes, silicones, metal peroxides, oils and/or emollients may be added.

In some embodiments, the particulate includes any suspended particle or group of particles added to mechanically scrub the skin of the consumer to aid in the cleansing process. The particulate may be used as a textural ingredient to modify the feel, spreadability or slip of a product. In some embodiments, the particulate includes vegetable meal-based polymers that have been made into a resin or other "plasticized" polymeric products which are then ground into various sizes. In some embodiments, soy meal may be used to form the vegetable meal based polymer particulate.

In some embodiments, the vegetable meal based polymers may be completely biodegradable. The vegetable meal based polymers may be a determined percentage of the composition. In some embodiments, the vegetable meal based polymers is formed with a predetermined half-life. In some embodiments, the vegetable meal based polymers is formed in a size of a predetermined mean diameter or predetermined weight.

Other objects and advantages of the present invention and/or of the currently preferred embodiments thereof will become more readily apparent in view of the following detailed description of the currently preferred embodiments and accompanying drawings.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

Figure 1:
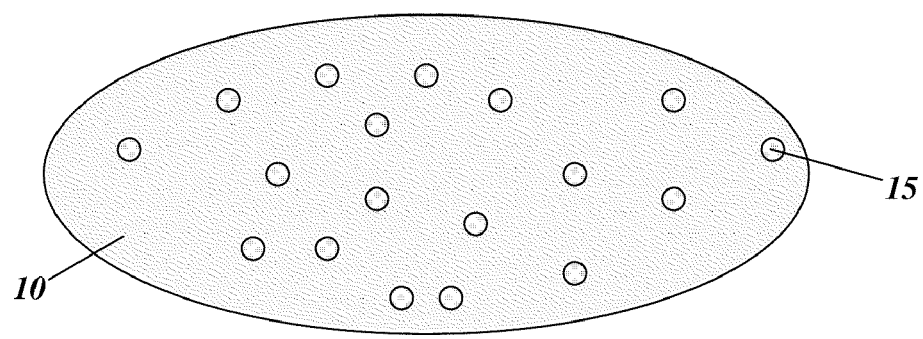
FIG. 1 is a schematic of one embodiment of particulate suspended in the media of a personal care formulation, according to the invention.

The present invention is directed to lathering, personal cleansing, and compositions providing superior cleansing with biodegradable components. In addition, the invention is directed to compositions for personal cleansing having biodegradable particulate.

A personal cleansing composition may include a surfactant, a thickener and particulate. In the following discussion, each of these ingredients will be discussed in turn. It will be understood, that a personal cleansing composition may include any combination or mixture of the ingredients discussed. Additionally, multiple ingredients may be used for the same purpose. In some embodiments, for example, more than one thickener may be used for the same or different purposes. Non-limiting examples of making these personal cleansing compositions are also provided.

While the cleansing compositions of this invention do not require a surfactant, preferred compositions contain one or more surfactants. When combined with water or mechanically agitated, the surfactant generates a foam or lather. Thus, the surfactant disperses the material to be cleansed or disinfected, increasing its surface area and enhancing its contact.

The surfactant used in the compositions of this invention may be a nonionic surfactant, an anionic surfactant, a cationic surfactant, an amphoteric surfactant or mixtures thereof. Examples of suitable nonionic surfactants are linear alkoxylates, an alkylphenol ethoxylate and polyoxypropylene-polyoxyethylene block copolymer. Non-limiting examples of anionic lathering surfactants include those selected from the group consisting of sarcosinates, sulfates, sulfonates, isethionates, taurates, phosphates, lactylates, glutamates, and mixtures thereof. In some embodiments, examples of preferred anionic lathering surfactants useful herein include those selected from the group consisting of sodium lauryl sulfate, ammonium lauryl sulfate, ammonium laureth sulfate, sodium laureth sulfate, sodium trideceth sulfate, ammonium cetyl sulfate, sodium cetyl sulfate, ammonium cocoyl isethionate, sodium lauroyl isethionate, sodium lauroyl lactylate, triethanolamine lauroyl lactylate, sodium caproyl lactylate, sodium lauroyl sarcosinate, sodium myristoyl sarcosinate, sodium cocoyl sarcosinate, sodium lauroyl methyl taurate, sodium cocoyl methyl taurate, sodium lauroyl glutamate, sodium myristoyl glutamate, and sodium cocoyl glutamate, soaps and mixtures thereof. Examples of suitable cationic surfactants are dodecyl ammonium chloride and cetyl dimethyl benzylammonium chloride. Examples of suitable amphoteric surfactants include alkyl betains or any surfactant with both a positive charge (commonly from ammonium) and a negative charge (commonly from a carboxylate, sulphonate or sulphate). In some embodiments, the surfactant includes one or more emulsifiers to stabilize an emulsion.

A thickener or thickening agent may also be used in the cleansing composition. By way of example, a thickener may include any one or combination of xanthan gum, carrageen gum, algae extracts, clays of various classes including but not limited to smectite and synthetic clays, carbomers, cross-linked silicones and polyethers, viscosifiers such as polyethylene glycols of various molecular weights and certain salts. In some embodiments, more than one thickener may be introduced to the composition. The thickener may be useful in providing body, increasing stability of the composition or improving the suspension of particulate as will be discussed in greater detail below.

In addition to the foregoing, the compositions of the invention may contain other additives such as perfumes, dyes, enzymes, silicones, metal peroxides, oils and/or emollients. For example, in some embodiments, one or more preservatives may be introduced to the composition to protect against microbial growth or contamination. Moreover, the shelf-life of the product may also be manipulated through the introduction of preservatives. Depending on the use of the composition, preservatives may be added to provide a shelf-life of approximately one to four years. In personal cleansing compositions, a two year shelf life may be desirable.

In some embodiments, particulate is introduced to the composition. The particulate may be any suspended particle or group of particles added to mechanically scrub the skin of the consumer to aid in the cleansing process. For example, when suspended in the composition, the particulate may be useful for cleansing, scrubbing and/or exfoliation. In some embodiments, the particulate is used as a textural ingredient to modify the feel, spreadability or slip of a product. In some embodiments, the particulate is used to modify the specific gravity of a product, for example as a filler. As used herein, the term particulate refers to micro or macro-sized free flowing particles of any shape. In additional to its role in exfoliation, the particulate may be used as a scrub or filler to add volume or weight to the composition. As previously discussed, the particulate has traditionally been formed of non-biodegradable polyethylene, leading to waste and environmental concerns, for example, its effect on marine life.

In some embodiments, vegetable meal based polymers may be made into a resin or other "plasticized" polymeric products which are then ground into various sizes. The ground byproduct may be introduced as particulate in a cleansing composition. Vegetable meal based polymer particulates are biodegradable and may be used in personal care, pet care and household products as a scrubbing, exfoliant or sensory product.

In some embodiments, soy meal may be used to form the vegetable meal based polymer particulate. Soy meal is generally a waste product of soy processors. Thus, two advantages are gained when soy meal is used. First, a useful purpose for soy meal is found and the unwanted soy meal is not discarded in landfills. Moreover, this unwanted soy meal may be used as particulate to replace amounts of polyethylene with a biodegradable polymer. Soy meal based polymers have been found stable in producing traditionally plastic products such as notebook covers and may exhibit the same stability for use in the area of personal cleansing. For example, the soy meal based polymer may replace polyethylene as an exfoliant (e.g., as particulate), scrubbing agent, sensory product or even as a filler. Vegetable meal based polymers in general may also replace non-biodegradable products such as nylon, boron nitride and clay as well as a number of categories of film formers, conditioners, plasticizers and silicone compounds in personal care, oral care, cosmetic, pet care and household products.

In personal care and cosmetics the soy meal based polymer may be used to replace portions of the current non-biodegradable polyethylene. The amount of soy meal based polymer used will depend on the type of personal care product (e.g., foot scrub, facial scrub, skin softener, body wash, body scrub, scalp scrub, toothpaste or as an exfoliant in pet care products). In some embodiments, the soy meal based polymer forms 0.001% to 30% of the composition. In some embodiments, the soy meal based polymer forms 0.001% to 5% of the composition. In at least some embodiments, the soy meal based polymer forms 0.1% to 2% of a cleansing composition. Because of its biodegradable characteristics, the half-life of the soy meal based polymer may be manipulated. For example, the soy meal based polymer may be produced in a manner to provide a half-life of four to ten years. In some embodiments, the soy meal based polymer has a half-life that is greater than the shelf-life of the product. In some embodiments, the soy meal based polymer has a half-life twice as along as the shelf-life of the product.

In addition, the particulate of the present invention may include various amounts of polyethylene in addition to the soy meal based polymer. For example, in some embodiments, the particulate includes 50% polyolefin (e.g., polyethylene). In at least some other embodiments, the particulate includes 10% to 50% polyolefin. In at least some embodiments, the particular includes 15% to 25% polyolefin. In at least some embodiments, the particulate includes no polyethylene or polyolefin. In such embodiments, a suitable compound or resin may be added to the soy meal based polymer to act as a backbone to increase stability and/or effectiveness of the particulate. In a least some embodiments, the particulate is formed with an amount of soy meal based polymer such that at least 40% of the composition is biodegradable. In some embodiments, the particulate is formed with an amount of soy meal based polymer such that at least 60% of the composition is biodegradable. In some other embodiments, the particulate is formed with an amount of soy meal based polymer such that at least 80% of the composition is biodegradable.

One significant improvement of the present composition is that the soy meal based particulate creates a much more pleasant odor profile than that created using only polyethylene particulate or other PVP film formers. In personal cleansing compositions and other personal care products, the odor profile is significant because the user typically chooses the product that smells best while shopping. Thus, a personal cleansing composition with an improved odor profile is desirable. The soy meal based particulate of the present invention provides the added and unexpected results of an improved odor profile as compared to traditional polyethylene particulate compositions.

As previously noted, the soy meal based polymer may be put through a grinding process to obtain particulate of a desired size. The size of the particulate may vary depending on the desired application. In some embodiments, the mean diameter of the pellets of the particulate is between 0.1 um and 1 cm. In some embodiments, the mean diameter of the pellets of the particulate is between 0.1 mm and 1 mm. In at least some embodiments, the mean diameter of the pellets of the particulate is between 0.2 mm and 0.6 mm. In addition to grinding, soy meal based particulate may also be formed in a number of ways including, but not limited to coacervation, extrusion, spheronization, shattering (e.g., ultrasound, irradiation, laser), drip on belt to form pastilles, or melt and drip/force through nozzles of different diameter. In some embodiments, the soy meal based polymer may also be used to make a powder. In some embodiments, the soy based polymer may also be used to make larger bead for visual aesthetics. In some embodiments the soy based polymer may also be used to make a film former.

After the grinding process, the particulate may be sifted or undergo a similar process to ensure that pellets are of the same or similar weight and/or size. In this manner, consistency may be maintained in the composition. Moreover, in some embodiments, pellets of different sizes or weight may be combined in the same composition. For example, pellets with a mean diameter of 5 mm may be added to the composition along with pellets of a mean diameter of 0.2 mm. Thus, the efficacy of the personal cleansing product may be adjusted by changing the mean diameter of the pellets. In some embodiments the particulates may be combined with other "exfoliants" including but not limited to: polyethylene, vegetable wax beads, wax beads, cellulosic beads, hpmc beads, alginate beads, agar, polymethymethacrylate beads, olive pit powder or the like to achieve the desired effect of exfoliation, cleansing or visual aesthetics.

FIG. 1 is a schematic of one embodiment of particulate suspended in the media of a personal care formulation. As seen in FIG. 1, the particulate 15 may be distributed throughout the media of a personal care formulation 10. The personal care formulation 10 may include any surfactant or thickener or combinations thereof as discussed above. The particulate 15 may be freely suspended in the media of the personal care formulation 10 for use as an exfoliant, a textural ingredient or for visual aesthetics.

Figure 2:
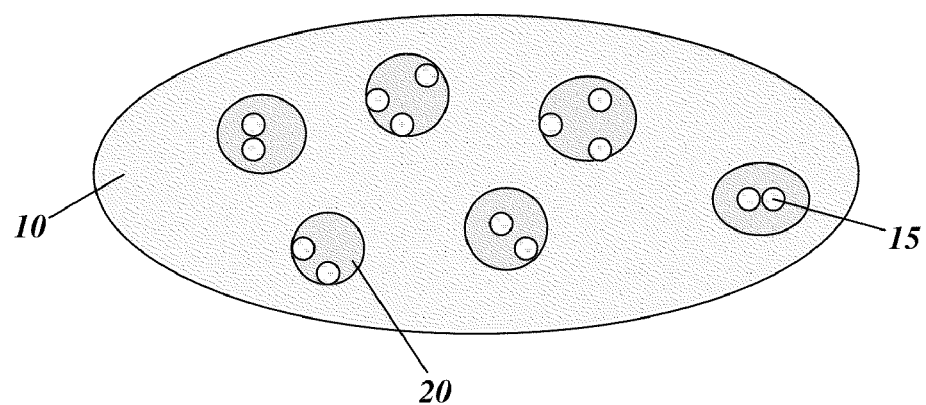
FIG. 2 is a schematic of another embodiment of encapsulated particulate suspended in the media of a personal care formulation, according to the invention.

FIG. 2 is a schematic of another embodiment of encapsulated particulate suspended in the media of a personal care formulation. As seen in FIG. 2, particulate 15 similar to that of FIG. 1 is distributed throughout the media of the personal care formulation 10. As shown in FIG. 2, the particulate 15 may be further encapsulated, entrapped, adsorbed or coacervated into another media to be delivered within a delivery media 20. As used herein, the term "encapsulate" includes all methods and configurations of introducing the particulate within a delivery media. In some embodiments, the delivery media 20 releases the particulate 15 upon contact with the skin or hair of the user.

Two formulations are disclosed herein as examples of cleansing compositions. It will be understood that the following formulations are introduced by way of example and are non-limiting. One of ordinary skill in the art will appreciate that the phases, ingredients and weight may be modified to yield other effective compositions.

EXAMPLE 1

Facial Cleansing Lotion with Traditional Polyethylene

| | PHASE | INGREDIENT | Q.S. % BY WEIGHT |
|---|---|---|---|
| 1 | A | Water | 45.55 |
| 2 | A | Carbomer | 0.25 |
| 3 | B | Ammonium Lauryl Sulfate | 4.0 |
| 4 | B | Sodium Lauryl Sulfate | 25.00 |
| 5 | B | Cocamidopropyl Betaine | 10.00 |
| 6 | C | Glycol Distearate | 1.50 |
| 7 | D | Cocamide MEA | 3.00 |
| 8 | D | Polyethylene | 0.30 |
| 9 | E | Caprylyl Glycol + Phenoxyethanol + Hexylene | 0.5 |

Water and a Carbomer are added and heated in phase A. The composition is mixed slowly in the CARBOPOL until fully dispersed (i.e, no fish eggs). The remaining phases are added in order, keeping phases A, B and C at approximately 70° C. The batch is cooled to 55° C. Phase D may then be added. The composition is mixed until uniform and the pH adjusted to 5.6 to 6.6.

EXAMPLE 2

Facial Cleansing Lotion with Soy Meal-Based Micronized Biodegradable Polymer

| | PHASE | INGREDIENT | Q.S. % BY WEIGHT |
|---|---|---|---|
| 1 | A | Water | 45.55 |
| 2 | A | Carbomer | 0.25 |
| 3 | B | Ammonium Lauryl Sulfate | 4.0 |
| 4 | B | Sodium Lauryl Sulfate | 25.00 |
| 5 | B | Cocamidopropyl Betaine | 10.00 |
| 6 | C | Glycol Distearate | 1.50 |
| 7 | D | Cocamide MEA | 3.00 |
| 8 | D | Soy Meal Based Micronized Polymer | 0.30 |
| 9 | E | Caprylyl Glycol + Phenoxyethanol + Hexylene | 0.5 |

The composition of Example 2 is a facial cleansing lotion with soy meal-based micronized biodegradable polymer. In Example 2, water and a Carbomer are added and heated in phase A. The composition is mixed slowly in the CARBOPOL until fully dispersed (i.e, no fish eggs). The remaining phases are added in order, keeping phases A, B and C at approximately 70° C. The batch is cooled to 55° C. In Example 2, 0.30% of soy meal based micronized polymer is added at phase D. Because the soy meal based polymer is biodegradable, the composition of Example 2 eliminates the environmental concerns of traditional compositions. Moreover, the composition of Example 2, as well as similar compositions effectively produces a stable composition suitable for personal cleansing solutions. Finally, the composition of Example 2 includes an unexpected improvement in the odor profile of the facial cleansing lotion.

As may be recognized by those skilled in the pertinent art based on the teachings herein, numerous changes and modifications may be made to the above-described and other embodiments of the present invention without departing from its scope as defined in the appended claims. Accordingly, this detailed description of preferred embodiments is to be taken in an illustrative, as opposed to a limiting sense.

What is claimed as new and desired to be protected by Letters Patent of the United States is:

1. A personal cleansing composition comprising:
   a surfactant for generating a lather;
   a thickener; and
   at least one particulate dispersed in the thickener, the at least one particulate comprising a soy meal-based polymer.

2. The personal cleansing composition of claim 1, further comprising at least one of a perfume, a dye, an enzyme, a silicone, an oil and an emollient.

3. The personal cleansing composition of claim 1, wherein the at least one particulate includes a group of suspended particles added to mechanically scrub the skin of a user.

4. The personal cleansing composition of claim 1, wherein the at least one particulate includes a group of suspended particles used as a textural ingredient to modify the feel, spreadability or slip of a product.

5. The personal cleansing composition of claim 1, wherein the at least one particulate is at least 80% biodegradable.

6. The personal cleansing composition of claim 1, wherein the at least one particulate is biodegradable and has a half-life of between about four years and about ten years.

7. The personal cleansing composition of claim 1, wherein the soy meal-based polymer forms between about 0.001% and about 30% of the composition.

8. The personal cleansing composition of claim 1, wherein the soy meal-based polymer forms between about 0.001% and about 5% of the composition.

9. The personal cleansing composition of claim 1, wherein the at least one particulate further includes polyethylene in addition to the soy meal-based polymer.

10. The personal cleansing composition of claim 1, wherein the soy meal-based polymer is ground to a predetermined size and configured and arranged to increase mechanical scrubbing efficacy.

11. The personal cleansing composition of claim 10, wherein the soy meal-based polymer is ground to pellets, the pellets having a mean diameter of between about 0.1 um and about 1 cm.

12. The personal cleansing composition of claim 10, wherein the soy meal-based polymer is ground to pellets, the pellets having a mean diameter of between about 0.1 mm and about 1 mm.

13. The personal cleansing composition of claim 1, wherein the at least one particulate is encapsulated within a delivery media, the delivery media being configured and arranged to release the at least one particulate upon contact with the skin or hair of a user.

14. A method of making a personal cleansing composition, comprising:
    providing a surfactant for generating a lather;
    introducing a thickener to provide body;
    dispersing at least one particulate in the thickener, the at least one particulate comprising a soy meal-based polymer.

15. The method of claim 14, further comprising the step of grinding the at least one particulate to pellets, the pellets having a mean diameter of between about 0.1 um and about 1 cm.

16. The method of claim 14, further comprising the step of encapsulating the at least one particulate within a delivery media, the delivery media being configured and arranged to release the at least one particulate upon contact with the skin of a user.

* * * * *